(12) United States Patent
Lin et al.

(10) Patent No.: US 10,813,906 B2
(45) Date of Patent: Oct. 27, 2020

(54) USE OF FERROUS AMINO ACID CHELATE TO TREAT INFECTION BY ENTEROPATHOGEN AND TO ENHANCE GROWTH PERFORMANCE

(71) Applicant: Profeat Biotechnology Co., Ltd., Taoyuan (TW)

(72) Inventors: Tsun-Yuan Lin, Taoyuan (TW); Mu-Kuei Chen, Taoyuan (TW); Kai-Ting Wang, Taoyuan (TW); Hsun-Jin Jan, Taoyuan (TW)

(73) Assignee: PROFEAT BIOTECHNOLOGY CO., LTD., Taoyuan (TW)

( * ) Notice: Subject to any disclaimer, the term of this patent is extended or adjusted under 35 U.S.C. 154(b) by 0 days.

(21) Appl. No.: 16/227,116

(22) Filed: Dec. 20, 2018

(65) Prior Publication Data

US 2019/0314322 A1 Oct. 17, 2019

Related U.S. Application Data

(60) Provisional application No. 62/657,083, filed on Apr. 13, 2018.

(51) Int. Cl.
| | | |
|---|---|---|
| *A61K 31/295* | (2006.01) | |
| *A61P 33/02* | (2006.01) | |
| *A61P 31/04* | (2006.01) | |
| *A23K 50/60* | (2016.01) | |
| *A23K 20/20* | (2016.01) | |
| *A23K 50/75* | (2016.01) | |
| *A23K 50/30* | (2016.01) | |
| *A23K 20/142* | (2016.01) | |

(52) U.S. Cl.
CPC .......... *A61K 31/295* (2013.01); *A23K 20/142* (2016.05); *A23K 20/30* (2016.05); *A23K 50/30* (2016.05); *A23K 50/60* (2016.05); *A23K 50/75* (2016.05); *A61P 31/04* (2018.01); *A61P 33/02* (2018.01)

(58) Field of Classification Search
CPC .............................. A61K 31/295; A61P 33/02
See application file for complete search history.

(56) References Cited

U.S. PATENT DOCUMENTS

| | | | |
|---|---|---|---|
| 2015/0065569 A1* | 3/2015 | Lin ...................... | A61K 31/295 514/502 |
| 2017/0224727 A1* | 8/2017 | Lin .......................... | A61K 9/08 |

\* cited by examiner

*Primary Examiner* — Samira J Jean-Louis
(74) *Attorney, Agent, or Firm* — Hamre, Schumann, Mueller & Larson, P.C.

(57) ABSTRACT

Disclosed herein is a method for treating infection by an enteropathogen and/or enhancing growth performance, which includes administering to a subject in need thereof a composition containing a ferrous amino acid chelate. Also disclosed herein is an animal feed containing the ferrous amino acid chelate.

2 Claims, No Drawings

Specification includes a Sequence Listing.

USE OF FERROUS AMINO ACID CHELATE TO TREAT INFECTION BY ENTEROPATHOGEN AND TO ENHANCE GROWTH PERFORMANCE

CROSS-REFERENCE TO RELATED APPLICATION

This application claims priority of U.S. Provisional Patent Application No. 62/657,083, filed on Apr. 13, 2018.

FIELD

The disclosure relates to a method for treating infection by an enteropathogen and/or enhancing growth performance with a ferrous amino acid chelate.

BACKGROUND

The presence of enteropathogen (including infection) in the small large intestines of an organism, which may cause enteritis and/or colitis, is of health concern. Common clinical manifestations associated with enteropathogen infection are frequent diarrhea, nausea, vomiting, abdominal pain, fever, chills, and other alterations of normal body conditions.

Common enteropathogens are bacterial enteropathogens (such as *Salmonella* spp., *Shigella* spp., *Escherichia coli*, *Campylobacter* spp., *Vibrio cholerae*, etc.); viral enteropathogens (such as enteroviruses, rotaviruses, Norwalk virus and adenoviruses); fungi (such as *Candida*); and parasitic enteropathogens (such as *Coccidia, Giardia lamblia, Balantidium coli, Blastocystis homnis, Cryptosporidium* spp., *Enterobius vermicularis* and *Entamoeba histolytica*).

Several prevention and treatment strategies, such as vaccination, administration of antibiotics or antiemetics, have been taken to combat enteropathogenic infection. However, there is still a need to further improve these prevention and/or treatment strategies.

The applicants' US Patent Publication No. 2017/0224727 A1 discloses a ferrous amino acid chelate, which is capable of stably passing through stomach, and which is effective in controlling body weight and enhancing lipid metabolism and lipolysis. In addition, the ferrous amino acid chelate can also be used in the treatment of cancer and diabetes, as well as to reduce the production of lactic acid by cancer cells, as disclosed in the applicants' previous patent applications, including US Patent Publication Nos. 2015/0065569 A1 and 2017/0007568 A1 and Taiwanese Invention Patent Publication No. 1587856. These patent applications and the granted patent are hereby incorporated by reference in their entirety.

SUMMARY

Accordingly, in a first aspect, the present disclosure provides a method for treating infection by an enteropathogen, which includes administering to a subject in need thereof a composition containing a ferrous amino acid chelate which includes ferrous ions and an amino acid.

According to a second aspect, this disclosure relates to an animal feed which includes the aforesaid ferrous amino acid chelate.

According to a third aspect, this disclosure provides a method for enhancing growth performance in an animal, which includes administering to the animal the above-mentioned composition and/or the above-mentioned animal feed.

DETAILED DESCRIPTION

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described. For clarity, the following definitions are used herein.

The term "treat" or "treatment" as used herein means lessening, inducing stasis of, or postponing or reducing the progression, development, onset, or severity of the disease or condition or severity of one or more symptoms associated with a disease or disorder or condition described herein, or ameliorating existing uncontrolled or unwanted symptoms, preventing additional symptoms, or relieving or alleviating the intensity and/or duration of a manifestation of a disorder experienced by a subject. The term "treat" also includes prophylactically preventing, curing, healing, altering, remedying, ameliorating, improving, or affecting a condition (e.g., a disease), the symptoms of the condition, or the predisposition toward the condition.

The present disclosure provides a method for treating infection by an enteropathogen, which includes administering to a subject in need thereof a composition containing a ferrous amino acid chelate and/or sintered ferrous amino acid particles prepared by sintering the ferrous amino acid chelate. The ferrous amino acid chelate includes ferrous ions and an amino acid.

According to this disclosure, the chelating ratio of the ferrous ions to the amino acid in the ferrous amino acid chelate ranges from 1:1 to 1:4. In certain embodiments, the chelating ratio of the ferrous ions to the amino acid in the ferrous amino acid chelate ranges from 1:1.5 and 1:2.5.

The process for preparing the ferrous amino acid chelate has been disclosed in, e.g. US 2017/0224727 A1 and includes the step of mixing a ferrous compound with an amino acid under heating. In certain embodiments, the mixing step may be conducted at a temperature ranging from 60° C. to 90° C. In certain embodiments, the mixing step may be conducted for 8 hours to 48 hours.

According to the disclosure, the weight ratio of the ferrous compound and the amino acid used in the preparation process is between 1:1.2 and 1:1.5. In an embodiment of this disclosure, the weight ratio of the ferrous compound and the amino acid is 1:1.3.

In certain embodiments, the ferrous compound may be ferrous sulfate, ferrous chloride, ferrous pyrophosphate, or combinations thereof.

In certain embodiments, the amino acid may be glycine. That is, the ferrous amino acid chelate may be ferrous glycinate chelate.

In certain embodiments, he sintered ferrous amino acid particles have an average particle size ranging from 500 to 2600 nm and a weight average molecular weight ranging from 1,500 Dalton to 600,000 Dalton.

In certain embodiments, the sintered ferrous amino acid particles have a weight average molecular weight ranging from 1,500 Dalton to 15,000 Dalton. In other embodiments, the sintered ferrous amino acid particles have a weight average molecular weight ranging from 400,000 Dalton to 550,000 Dalton.

In an exemplary embodiment, the sintered ferrous amino acid particles have an average particle size (which is measured, e.g., in water by dynamic light scattering (DLS) on Beckman Coulter N5 Submicron Particle Size Analyzer) of about 1465.90±132.29 nm. In addition, the number-average molecular weight (Mn), weight-average molecular weight (Mw), peak molecular weight (MP) and polydispersity (PDI) of the sintered ferrous amino acid particles dissolved in water, determined by gel permeation chromatography using Waters Alliance 2695 System, are around 68188 Dalton, 525538 Dalton, 286426 Dalton and 7.707205, respectively.

As used herein, the term "subject" refers to any animal of interest, suchashumans, monkeys, cows, sheeps, horses, pigs, chickens, goats, dogs, cats, mice and rats. In certain embodiments, the subject may be a chicken.

In certain embodiments, the enteropathogen may be a bacterial enteropathogen. Examples of bacterial enteropathogen include, but are not limited to, *Campylobacter* spp., *Clostridium perfringens, Escherichia coli* (such as enteropathogenic *E. coli* (EPEC), enteroinvasive *E. coli* (EIEC), enteroaggregative *E. coli* (EAEC), enterotoxigenic *E. coli* (ETEC), etc.), *Listeria monocytogenes, Vibrio cholerae, Salmonella* spp., and *Staphylococcus aureus*.

Examples of *Campylobacter* strains include, but are not limited to, *Campylobacter jejuni, Campylobacter coli, Campylobacter lari* and *Campylobacter upsaliens*.

Examples of *Salmonella* strains include, but are not limited to, *Salmonella enterica, Salmonella bongori*, and the subspecies thereof. *Salmonella* enteric is a type of species and is further divided into six subspecies (i.e., *S. enterica* subsp. *Arizonae, S. enterica* subsp. *Diarizonae, S. enterica* subsp. *Enteric, S. enterica* subsp. *Houtenae, S. enterica* subsp. *Indica, S. enterica* subsp. *Enteritidis* and *S. enterica* subsp. *Salamae*) that include over 2500 serotypes, such as *Salmonella Gallinarum, Salmonella Pullorum, Salmonella Choleraesuis, Salmonella Dublin, Salmonella Enteritidis, Salmonella Heidelberg, Salmonella Paratyphi, Salmonella Typhi*, and *Salmonella Typhimurium*.

In certain embodiments, the enteropathogen may be a parastic enteropathogen. Examples of parastic enteropathogen include, but are not limited to, *Coccidia, Giardia, Enterobius vermicularis, Entamoeba histolytica, Cryptosporidium* spp., *Balantidium coli, Blastocystis hominis* and *Cyclospora*.

The composition according to this disclosure may be prepared in the form of a pharmaceutical composition or a food composition.

If the composition is prepared in the form of the pharmaceutical composition, the composition may further include a pharmaceutically acceptable carrier, and made into a dosage form suitable for oral administration using technology well-known to those skilled in the art. Examples of the dosage form include, but are not limited to, solution, suspension, emulsion, powder, tablet, pill, syrup, lozenge, troche, chewing gum, capsule, slurry and the like.

Examples of the pharmaceutically acceptable carrier suitable for use in this disclosure may include, but are not limited to, solvent, emulsifier, suspending agents, decomposers, binding agents, excipients, stabilizing agents, chelating agents, diluents, gelling agents, preservatives, lubricants, absorption delaying agents, liposomes, and combinations thereof.

The composition according to this disclosure may be in the form of a food additive (an exemplary example of the food composition), which can be added into an edible material to prepare a food product for animal consumption. Examples of the food product according to this disclosure may include, but are not limited to, fluid milk products (e.g., milk and concentrated milk), health foods, animal feeds and dietary supplements.

The applicants further added the aforesaid ferrous amino acid chelate to an animal feed and fed chickens and postweaning piglets with the animal feed. It is verified from the experimental results that: the ferrous amino acid chelate according to this disclosure is capable of effectively enhancing growth performance of the animals.

Thereofore, this disclosure provides an animal feed containing the aforementioned ferrous amino acid chelate and/or the sintered ferrous amino acid particles obtained therefrom.

The present disclosure also provides a method for enhancing growth performance in an animal, which includes administering to the animal the above-mentioned animal feed.

The term "growth performance" as used herein refers to growth rate, body weight and/or feed efficiency.

In certain embodiments, the ferrous amino acid chelate of this disclosure and/or the sintered ferrous amino acid particles obtained therefrom can be added to an animal feed using a standard technique well known to one of ordinary skill in the art. For instance, the ferrous amino acid chelate and/or the sintered ferrous amino acid particles may be directly added to an animal feed, ormaybeutilizedtobepreparedasan intermediate composition (e.g., a feed additive or a premix) suitable to be subsequently added to an animal feed. In certain embodiments, the animal feed of this disclosure is prepared by mixing the ferrous amino acid chelate and an animal basal diet together.

The animal feed according to this disclosure may be orally administrable, and can be formulated into a form, including, but not limited to, liquid form, solid form (such as powder form, granular form, particulate form, or a compressed tablet), gel form, and slurry form, by virtue of a technique well known to one of ordinary skill in the art.

This disclosure will be further described by way of the following examples. However, it should be understood that the following examples are solely intended for the purpose of illustration and should not be construed as limiting the disclosure in practice.

EXAMPLES

General Experimental Materials:
1. Preparation of Ferrous Amino Acid Chelate:

The ferrous amino acid chelate was prepared based on the procedure as disclosed in Preparation Example 1 of US 2017/0224727 A1. Specifically, ferrous sulfate was mixed with glycine (above 98% purity) in a weight ratio of 1:1.3, followed by heating from 60° C. to 90° C. for 8 hours to 48 hours, so as to obtain the ferrous amino acid chelate for further experiments as described below. The chelating ratio of the ferrous irons to the amino acid in the obtained ferrous amino acid chelate was between 1:1 and 1:4.

Example 1

Experimental Procedures:

Taiwan black-feather country chickens (1 day of age) were purchased from Animal Research Farm in National Chia-Yi University (Taiwan), and were raised in a farm under the guidelines of Animal Care Committee of the Council of Agriculture, Taiwan. The experimental chickens were randomly divided into a control group and an experimental group (n=40/group), and each group was placed in a pen with a size of 6.5 m². Water was provided ad libitum for all of the experimental chickens.

Each of the experimental chickens was fed with a mixed feed for 12 weeks at a dose of 0.1 kg per day. The mixed feed supplied to the control group was made from a basal diet and a ferrous sulfate (20 g of Fe per 1000 kg of the mixed feed). The mixed feed supplied to the experimental group was made from the basal diet and the ferrous amino acid chelate prepared as described in the section, entitled "1. Preparation of ferrous amino acid chelate" of the "General Experimental Materials" (20 g of Fe per 1000 kg of the mixed feed).

The body weight of each chicken was determined before and after supply of the mixed feed. Subsequently, average daily gain (ADG) of the chickens in each group was calculated based on the body weight and the feed intake. Feed efficiency (FE) defined as a ratio of total feed intake to total body weight was also calculated. The experimental data were analyzed via Student's t-test so as to assess the difference between the test groups. Statistical significance is indicated by $p<0.05$.

Moreover, during supply of the mixed feed, fifteen chickens were randomly chosen at a designated time point to collect the feces from the cloaca thereof using cotton swabs.

*Coccidia* infestation is determined by microscopic observation of the obtained feces sample.

In addition, the obtained feces were subjected to nucleic acid extraction with Taco™ DNA/RNA Extraction Kit (GeneReach Biotechnology Corp) according to the manufacturer's instructions. The thus obtained DNA sample, which served as a template, was used to conduct real time polymerase chain reaction (PCR). Specifically, the real time PCR experiment was performed in a 20 μL reaction mixture containing 5 μL of template, 1.2 μL of each primer (10 μM), 0.5 μL of probe (10 μM), 10 μL of reaction buffer (TaqMan® Universal Master Mix II with UNG, Applied Biosystems), and 2.1 μL of ddH$_2$O. The primers and probe for detecting the respective one of the enteropathogens are listed in Table 1.

TABLE 1

| Enteropathogens | Primers/probe | Sequence (5'→3') |
|---|---|---|
| *Escherichia coli* | Forward primer | ttatagcgacagcaccaaatatg (SEQ ID NO: 1) |
| | Reverse primer | cacgataccatccatatatctgag (SEQ ID NO: 2) |
| | Probe | ttccacctaacgcagaaacctcct (SEQ ID NO: 3) |
| *Salmonella* spp. | Forward primer | ctcaccaggagattacaacatgg (SEQ ID NO: 4) |
| | Reverse primer | agctcagaccaaaagtgaccatc (SEQ ID NO: 5) |
| | Probe | caccgacggcgagaccgactt (SEQ ID NO: 6) |
| *Clostridium perfringens* | Forward primer | ggcaaagaggaaattataaacaagct (SEQ ID NO: 7) |
| | Reverse primer | gcgctatcaacggcagtaaca (SEQ ID NO: 8) |
| | Probe | atactccatatcatcctgc (SEQ ID NO: 9) |

Note:
5'-end and 3'-end of the probe were labeled with Fluorescein amidite (FAM) and Black Hole Quencher-1 (BHQ ®-1), respectively.

Each sample in the PCR tube was pre-incubated at 55° C. for 2 minutes and then at 95° C. for 10 minutes during the initiation process to activate the DNA polymerase, followed by 45 cycles of denaturation at 95° C. for 15 seconds and primer annealing and DNA elongation at 60° C. for 60 seconds.

Results:

The experimental results with respect to the growth performance and enteropathogen infection were shown in Table 2.

TABLE 2

| Time point | Control group | Experimental group |
|---|---|---|
| Growth performance | | |
| Body weight (g) [1] Week 0 | 31.06 ± 2.94 | 32.48 ± 3.49 |
| Week 12 | 1965 ± 194.44 | 2143.71 ± 250.23* |
| ADG (g/day per chicken) Week 12 | 23.3 | 25.44 |
| FE Week 12 | 3.88 | 3.59 |
| Enteropathogen infection[2] | | |
| *Escherichia coli* Week 10 | 93% | 27% |
| *Salmonella* spp. Week 10 | 93% | 53% |
| *Clostridium perfringens* Week 6 | 33% | 0% |
| Coccidia Week 6 | 100% | 33% |

[1] shown as mean ± standard deviation (S.D.)
[2] shown as percentage of infection among 15 selected chickens
*$p < 0.05$ when compared with the comparative group It can be seen from Table 2 that the body weight of the chickens in the experimental group is significantly higher than that of the chickens in the control group after supply of the mixed feed. ADG and FE with respect to the experimental group are respectively superior than ADG and FE with respect to the control group. In addition, as compared to the control group, the percentage of infection for each of the tested enteropathogens is significantly lower in the experimental group. The above results indicate that the mixed feed containing the ferrous amino acid chelate of this disclosure is able to effectively reduce the infection by enteropathogens and to enhance the growth performance of the chickens.

Example 2

Experimental Procedures:

About 1000 male piglets and 1000 female piglets (purchased from HAIFUNG ranch, Yunlin County, Taiwan and bred in the nursery) were used in the following experiment. The experimental piglets were randomly divided into an experimental group and a control group, and sufficient water and feed were supplied to the experimental piglets.

After weaning (i.e., at the age of 4 weeks), each of the experimental piglets was fed with a mixed feed for 8 weeks until the experimental piglets reached the age of 12 weeks. The mixed feed supplied to the control group was made from a basal diet and a ferrous sulfate in a weight ratio of 1000:1. The mixed feed supplied to the experimental group was made from the basal diet and the ferrous amino acid chelate prepared as described in the section, entitled "1. Preparation of ferrous amino acid chelate" of the "General Experimental Materials", in a weight ratio of 1000:1.

At the age of 4 and 12 weeks, total feed intake and the body weight of the postweaning piglets in each group were measured and recorded. Subsequently, average daily gain (ADG) and average daily feed intake (ADFI) of the postweaning piglets in each group were calculated based on the body weight and the total feed intake. Feed efficiency (FE) defined as a ratio of ADFI to ADG was also calculated. The experimental results are shown in Table 3.

The experimental data were expressed as mean±S.D., and were analyzed via Student's t-test so as to assess the difference between the test groups. Statistical significance is indicated by $p<0.05$.

Results:

TABLE 3

| Growth performance | | Control group | Experimental group |
|---|---|---|---|
| Body weight (kg)[1] | 4 weeks | 8.40 ± 1.17 | 9.08 ± 0.94* |
| | 12 weeks | 28.00 ± 4.28 | 32.84 ± 4.01* |
| Total feed intake (kg) | | 33,255 | 36,500 |
| ADG (kg/day per piglet) | | 0.30 | 0.40 |
| ADFI (kg/day per piglet) | | 0.85 | 0.78 |
| FE | | 2.80 | 1.93 |

[1] shown as mean ± S.D.
*p < 0.05 when compared with the control group

Referring to Table 3, the body weight of the postweaning piglets in the experimental group is significantly higher than that of the postweaning piglets in the control group at the piglets' age of 12 weeks. In addition, ADG of the postweaning piglets in the experimental group is higher than ADG of the postweaning piglets in the control group, and FE with respect to the experimental group is significantly lower (i.e., superior) than FE with respect to the control group.

The above experimental results indicate that the mixed feed containing the ferrous amino acid chelate of this disclosure is able to effectively enhance the growth performance of the postweaning piglets.

All patents and literature references cited in the present specification as well as the references described therein, are hereby incorporated by reference in their entirety. In case of conflict, the present description, including definitions, will prevail.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for reducing an infection due to an enteropathogen, comprising administering to a subject in need thereof a composition containing a ferrous amino acid chelate that includes a ferrous ion and an amino acid, wherein the ferrous amino acid chelate is a ferrous glycinate chelate, and the enteropathogen is *Coccidia*.

2. The method of claim 1, wherein the ferrous amino acid chelate has a ratio of the ferrous ion to the amino acid in a range of 1:1 to 1:4.

* * * * *

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: Forward primer for detecting E. coli

<400> SEQUENCE: 1
ttatagcgac agcaccaaat atg                                           23

<210> SEQ ID NO 2
<211> LENGTH: 24
<212> TYPE: DNA
<213> ORGANISM: Artificial Sequence
<220> FEATURE:
<223> OTHER INFORMATION: Reverse primer for  detecting E. coli

<400> SEQUENCE: 2
cacgatacca tccatatatc tgag                                          24

<210> SEQ ID NO 3
<211> LENGTH: 24
<212> TYPE: DNA
<213> ORGANISM: Artificial Sequence
<220> FEATURE:
<223> OTHER INFORMATION: Probe for detecting E. coli

<400> SEQUENCE: 3
```
ttccacctaa cgcagaaacc tcct                                        24

<210> SEQ ID NO 4
<211> LENGTH: 23
<212> TYPE: DNA
<213> ORGANISM: Artificial Sequence
<220> FEATURE:
<223> OTHER INFORMATION: Forward primer for detecting Salmonella spp.

<400> SEQUENCE: 4
ctcaccagga gattacaaca tgg                                         23

<210> SEQ ID NO 5
<211> LENGTH: 23
<212> TYPE: DNA
<213> ORGANISM: Artificial Sequence
<220> FEATURE:
<223> OTHER INFORMATION: Reverse primer for detecitng Salmonella spp.

<400> SEQUENCE: 5
agctcagacc aaaagtgacc atc                                         23

<210> SEQ ID NO 6
<211> LENGTH: 22
<212> TYPE: DNA
<213> ORGANISM: Artificial Sequence
<220> FEATURE:
<223> OTHER INFORMATION: Probe for detecting Salmonella spp.

<400> SEQUENCE: 6
caccgacggc gagaccgact tt                                          22

<210> SEQ ID NO 7
<211> LENGTH: 26
<212> TYPE: DNA
<213> ORGANISM: Artificial Sequence
<220> FEATURE:
<223> OTHER INFORMATION: Forward primer for detecting C. perfringens

<400> SEQUENCE: 7
ggcaaagagg aaattataaa caagct                                      26

<210> SEQ ID NO 8
<211> LENGTH: 21
<212> TYPE: DNA
<213> ORGANISM: Artificial Sequence
<220> FEATURE:
<223> OTHER INFORMATION: Reverse primer for detecting C. perfringens

<400> SEQUENCE: 8
gcgctatcaa cggcagtaac a                                           21

<210> SEQ ID NO 9
<211> LENGTH: 19
<212> TYPE: DNA
<213> ORGANISM: Artificial Sequence
<220> FEATURE:
<223> OTHER INFORMATION: Probe for detecting C. perfringens

<400> SEQUENCE: 9
atactccata tcatcctgc                                              19